United States Patent [19]

Biller et al.

[11] Patent Number: 5,157,146
[45] Date of Patent: Oct. 20, 1992

[54] METHOD FOR PREPARING ISOPRENOID CYCLOPROPANE 1,1-DICARBOXYLATES

[75] Inventors: Scott A. Biller, Ewing, N.J.; Cornelia Forster, Bensalem, Pa.

[73] Assignee: E. R. Squibb & Sons, Inc., Princeton, N.J.

[21] Appl. No.: 782,193

[22] Filed: Oct. 24, 1991

Related U.S. Application Data

[63] Continuation-in-part of Ser. No. 573,507, Aug. 27, 1990, Pat. No. 5,095,136.

[51] Int. Cl.$^5$ .............................................. C07C 69/74
[52] U.S. Cl. ................................................... 560/124
[58] Field of Search .......................................... 560/124

[56] References Cited

U.S. PATENT DOCUMENTS

| | | | |
|---|---|---|---|
| 3,445,499 | 5/1969 | Martel | 560/124 |
| 3,658,879 | 4/1972 | Julia | 560/124 |
| 3,997,586 | 12/1976 | Martel | 560/124 |
| 4,113,969 | 9/1978 | Lantzsch | 560/124 |
| 4,305,885 | 12/1981 | Hanack | 260/464 |
| 4,307,244 | 12/1981 | Ficini | 560/124 |
| 4,401,601 | 8/1983 | Martel | 560/124 |
| 4,642,372 | 2/1987 | Martel | 560/124 |

FOREIGN PATENT DOCUMENTS

| | | | |
|---|---|---|---|
| 49-66660 | 6/1974 | Japan | 560/124 |

OTHER PUBLICATIONS

Martel, J. et al, Bull. Soc. Chim. Fr. 1967, 985, DAS 1289046 (1969).

Arlt, D. et al, "Syntheses of Pyrethroid Acid," Angew. Chem. Int. Ed. Engl. 20, No. 9, 703–722 (Sep. 1981).

Campbell, R. V. M. et al, "Synthesis of (±)-Presqualene Alcohol, (±)-Prephytoene Alcohol, and Structurally Related Compounds," J.C.S. Perkin I, 1975, 897–913.

Hendrickson, J. B. et al, J. Am. Chem. Soc. 1974, 95, 2275–2276.

Capson, T. L., et al, "Synthesis of Ammonium Analogues of Carbocationic Intermediates in the Conversion of Presqualene Diphosphate to Squalene," J. Org. Chem. 1988, 53, 5903–5908.

Poulter, C. D., et al, "Squalene Synthetase. Inhibition by Ammonium Analogues of Carbocationic Intermediates in the Conversion of Presqualene Diphosphate to Squalene," J. Am. Chem. Soc. 1989, 111, 3734–3739.

Julia, M. et al, Guy-Rouault Bull. Soc. Chim. Fr. 1967, 1411.

Primary Examiner—Michael L. Shippen
Attorney, Agent, or Firm—Burton Rodney

[57] ABSTRACT

A process is provided for preparing isoprenoid cyclopropane 1,1-dicarboxylates which are useful in preparing squalene synthetase inhibitors which inhibit cholesterol biosynthesis, and also useful in preparing pyrethrin insecticides.

10 Claims, No Drawings

METHOD FOR PREPARING ISOPRENOID CYCLOPROPANE 1,1-DICARBOXYLATES

REFERENCE TO OTHER APPLICATIONS

This application is a continuation-in-part of application Ser. No. 573,507, filed Aug. 27, 1990, now U.S. Pat. No. 4,095,136.

FIELD OF THE INVENTION

The present invention relates to a method for preparing isoprenoid cyclopropane 1,1-dicarboxylates which are useful in preparing squalene synthetase inhibitors which inhibit cholesterol biosynthesis, and also useful in preparing pyrethrin insecticides.

BACKGROUND OF THE INVENTION

Martel, J. et al, Bull. Soc. Chim. Fr. 1967, 985, DAS 1289046 (1969), Arlt, D. et al, "Syntheses of Pyrethroid Acid," Angew. Chem. Int. Ed. Engl. 20, No. 9, 703–722 (Sep. 1981), at page 707 and Campbell, R.V.M. et al, "Synthesis of (±)-Presqualene Alcohol, (±)-Prephytoene Alcohol, and Structurally Related Compounds," J. C. S. Perkin I, 1975, 897–913, disclose the reaction of phenylsulfones with unsaturated monoesters to form transchrysanthemic acid esters according to the following reactions (Arlt et al).

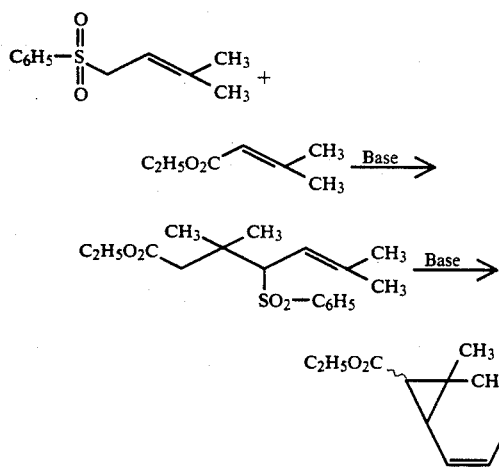

and to form presqualene and prephytoene systems (Campbell et al).

U.S. Pat. No. 4,305,885 describes the preparation of chrysanthemate derivatives via the addition of a perfluorobutyl sulfone to an unsaturated monoester according to the following reaction sequence:

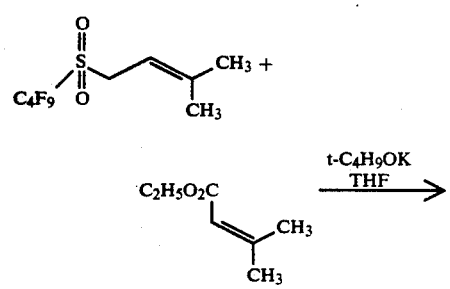

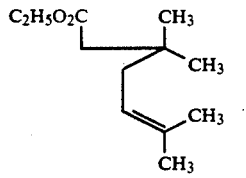

Julia, M. et al Guy-Rouault Bull. Soc. Chim. Fr. 1967, 1411 discloses the cyclopropanation of a 1,1-cyclopropane dicarboxylic ester with a phenyl sulfone according to the following reaction

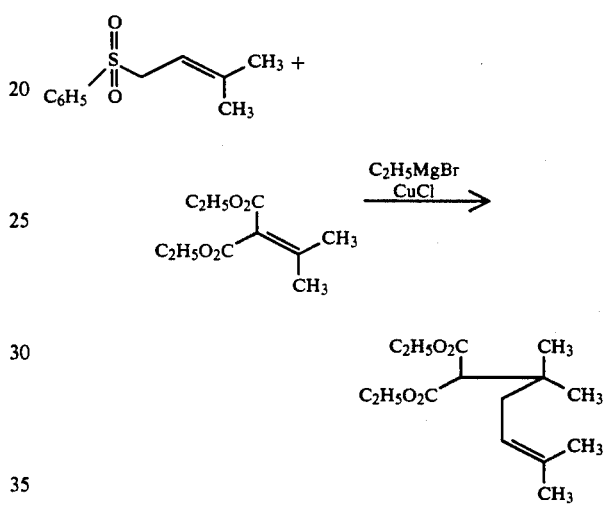

Hendrickson, J. B. et al, J. Am. Chem. Soc. 1974, 95 2275–2276 disclose the conjugate addition of trifluoromethyl sulfones to unsaturated ketones followed by elimination to provide cyclopropanes in a separate step as outlined below.

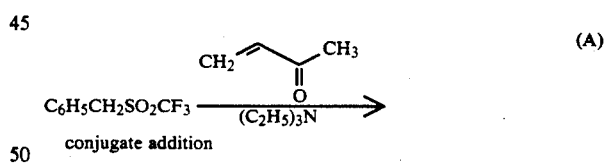

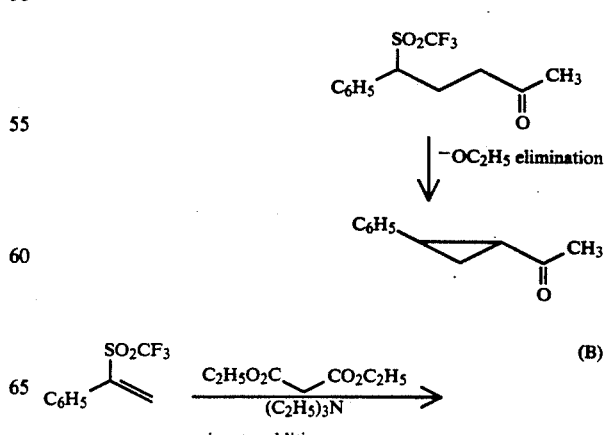

-continued

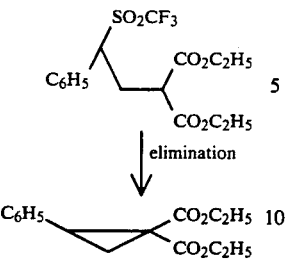

Capson, T. L., et al, "Synthesis of Ammonium Analogues of Carbocationic Intermediates in the Conversion of Presqualene Diphosphate to Squalene," J. Org. Chem. 1988, 53, 5903-5908 disclose the preparation of certain squalene synthetase inhibitors of the structure

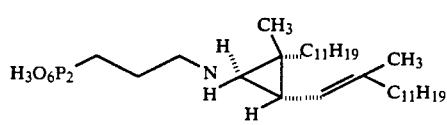

which are prepared from an isoprenoid cyclopropane monocarboxylate of the structure

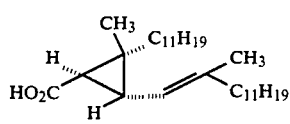

Poulter, C. D. et al, "Squalene Synthetase. Inhibition by Ammonium Analogues of Carbocationic Intermediates in the Conversion of Presqualene Diphosphate to Squalene," J. Am. Chem. Soc. 1989, 11, 3734-3739, disclose the testing of such squalene synthetase inhibitors.

DESCRIPTION OF THE INVENTION

In accordance with the present invention, a method is provided for preparing isoprenoid cyclopropane 1,1-dicarboxylates, which method is simple, clean and efficient and produces product in substantially pure form.

The method of the invention for preparing isoprenoid cyclopropane 1,1-dicarboxylates of the structure

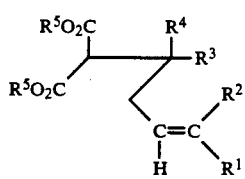   I wherein $R^1$, $R^2$, $R^3$ and $R^4$ are the same or different and are independently selected from $CH_3$ or

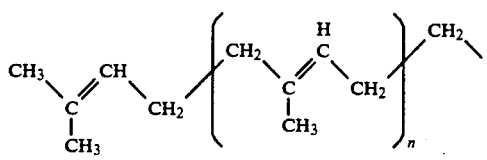

n is 0 to 3, and $R^5$ is lower alkyl, includes the step of pretreating an allylic fluorinated sulfone of the structure II

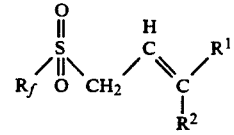

wherein $R_f$ is $CF_3(CF_2)_m$ where m is 0 to 5, and $R^1$ and $R^2$ are as defined above with a base at a reduced temperature of from about $-80$ to about $-40°$ C., to form the corresponding carbanion α to the sulfone having the structure

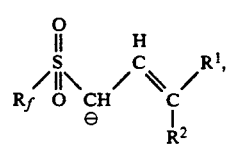   IIA reacting IIA with an alkene 1,1-dicarboxylate of the structure

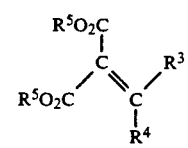   III wherein $R^3$, $R^4$ and $R^5$ are as defined above, at a reduced temperature of within the range of from about $-80°$ to about $-40°$ C., to form the intermediate IIIA

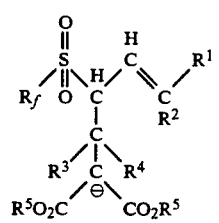   IIIA and subjecting IIIA to an increasing temperature of within the range of from about 25° to 0° C. to form I.

The starting allylic fluorinated sulfone II may be prepared by treating an allylic halide of the structure IV

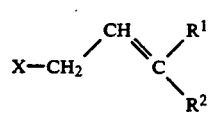   IV wherein $R^1$ and $R^2$ are as defined above, and X is Br, Cl or I (preferably Br) with a triflinate of the structure V

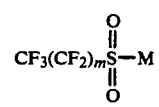   V wherein M is an alkali metal such as K, Na or Li, (K preferred) optionally in the presence of 18-crown-6 or 15-crown-5, and an inert organic solvent such as dimethylformamide (DMF), dimethylsulfoxide (DMSO), hexamethylphosphoramide (HMPA), tetrahydrofuran (THF) or mixtures thereof.

In the method of the invention for preparing isoprenoid cyclopropane 1,1-dicarboxylate I, the allylic fluorinated sulfone II is treated with a strong base such as n-butyllithium or lithium diisopropylamide, preferably n-butyllithium in an inert organic solvent, such as hexane, and an anion activator, namely, HMPA or N,N'-dimethylpropyleneurea (DMPU), preferably HMPA (which activates the anion of sulfone II towards conjugate addition). The above reaction is carried out in the presence of an inert organic solvent such as tetrahydrofuran, diethyl ether, preferably tetrahydrofuran, at reduced temperature of within the range of from about −80° C. to about −40° C., and preferably from about −78° C. to about −50° C. under an inert atmosphere such as argon or nitrogen, preferably argon.

The so-formed carbanion IIA is reacted with alkene 1,1-dicarboxylate III in the presence of an inert organic solvent such as tetrahydrofuran, diethyl ether, preferably tetrahydrofuran at a reduced temperature of within the range of from about −80° C. to about −40° C., preferably from about −78° C. to about −50° C., preferably under an inert atmosphere such as argon, for a period of from about 0.1 to about 2 hours to form the intermediate IIIA. Without isolating IIIA, the reaction mixture is subjected to increasing temperatures of within the range of from about 25° to about 0° C. for a period of from about 0.5 to about 7 hours to form dicarboxylate I.

The allylic fluorinated sulfone II will be employed in a molar ratio to the alkene 1,1-dicarboxylate III within the range of from about 0.7:1 to about 1.3:1.

The base will be employed in a molar ratio to sulfone II of within the range of from about 0.9:1 to about 1.1:1, while the sulfone anion activator will be employed in a molar ratio to sulfone II of within the range of from about 1:1 to about 5:1, and preferably about 2:1.

Where $R^3$ and $R^4$ in the alkene 1,1-dicarboxylate II differ, an isomeric mixture of product will be obtained which may be separated by conventional procedures such as crystallization or chromatography to give the desired isomer.

The above method produces an unexpectedly high yield of substantially clean product in a single step with minimal side products. This is attributed to the formation of intermediate adduct IIIA which forms at low temperatures of from about −80° to about −40° C. substantially without formation of undesirable side products regardless of whether only one of $R^3$ and $R^4$ is methyl. The use of high temperatures in reacting IIA and III would cause reduced yields and formation of undesirable side products especially when only one of $R^3$ and $R^4$ is methyl.

The pretreatment of sulfone II with base to form the carbanion of II insures that all base is reacted before the alkene 1,1-dicarboxylate III is added. In this manner, formation of undesirable side products is substantially reduced.

The starting alkene 1,1-dicarboxylate III may be prepared as disclosed in the copending parent application Ser. No. 573,507, filed Aug. 27, 1990, now U.S. Pat. No. 5,095,136.

The starting allylic fluorinated sulfone II may be prepared by reacting allylic halide IV with triflinate V in the presence of 18-crown-6 or 15-crown-5 and an inert organic solvent such as dimethylformamide, DMSO, HMPA, THF or mixtures thereof, employing a molar ratio of IV:V of within the range of from about 0.7:1 to about 1.2:1.

The allylic halide may be prepared as described in U.S. Pat. No. 4,871,721, for example, as described in Example 1, Part A.

Examples of starting allylic halides IV which may be employed herein include, but are not limited to, the following:

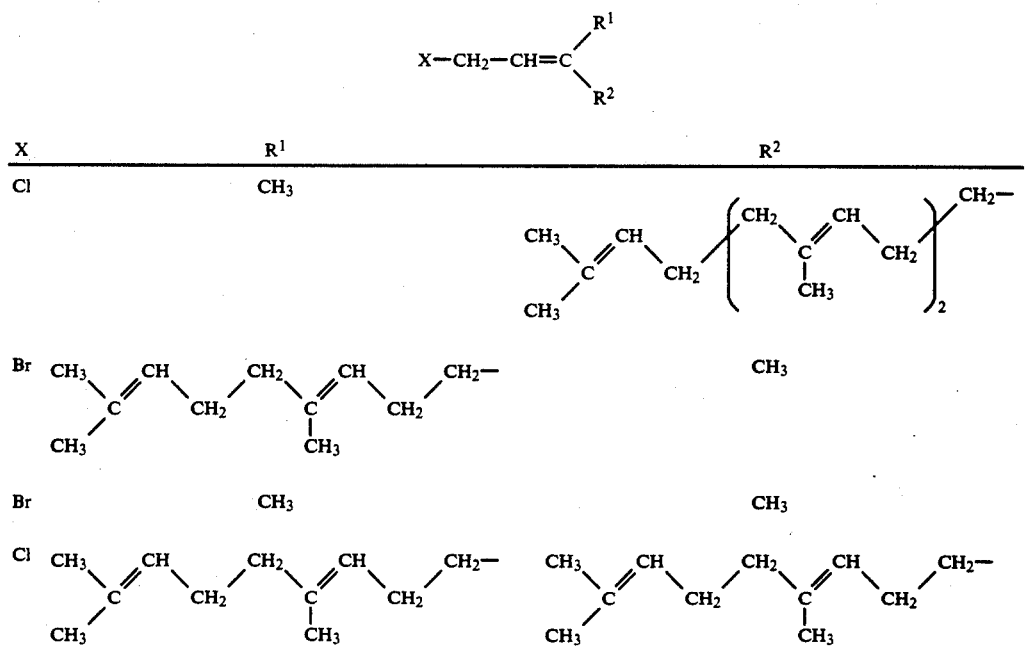

$$X-CH_2-CH=C\begin{array}{c}R^1\\R^2\end{array}$$

| X | $R^1$ | $R^2$ |
|---|---|---|
| Cl | $CH_3$ | 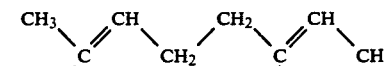 |
| Br |  |  |
| Br | $CH_3$ |  |

Examples of starting triflones V which may be employed herein include, but are not limited to, the following:

$$CH_3(CF_2)_m-\underset{\underset{O}{\|}}{\overset{\overset{O}{\|}}{S}}-M$$

| m | M |
|---|---|
| 0 | K |
| 1 | Na |
| 2 | K |

$$CH_3(CF_2)_m-\underset{\underset{O}{\|}}{\overset{\overset{O}{\|}}{S}}-M$$

| m | M |
|---|---|
| 3 | K |
| 4 | Li |
| 5 | K |

Examples of starting alkene 1,1-dicarboxylates III which may be employed herein include, but are not limited to, the following:

$$\begin{array}{c}R^5O_2C\\R^5O_2C\end{array}C=C\begin{array}{c}R^3\\R^4\end{array}$$

| $R^5$ | $R^3$ | $R^4$ |
|---|---|---|
| $CH_3$ | $CH_3$ | $CH_3$ |
| $C_2H_5$ | $CH_3$ | 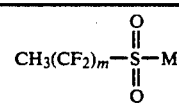 |
| $CH_3$ | 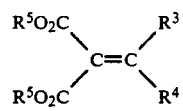 | 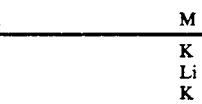 |
| $C_2H_5$ | 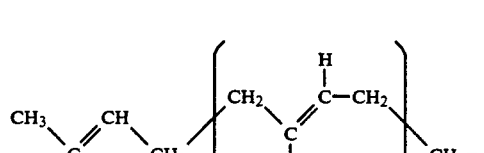 | 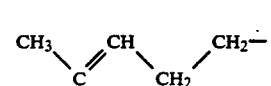 |

-continued

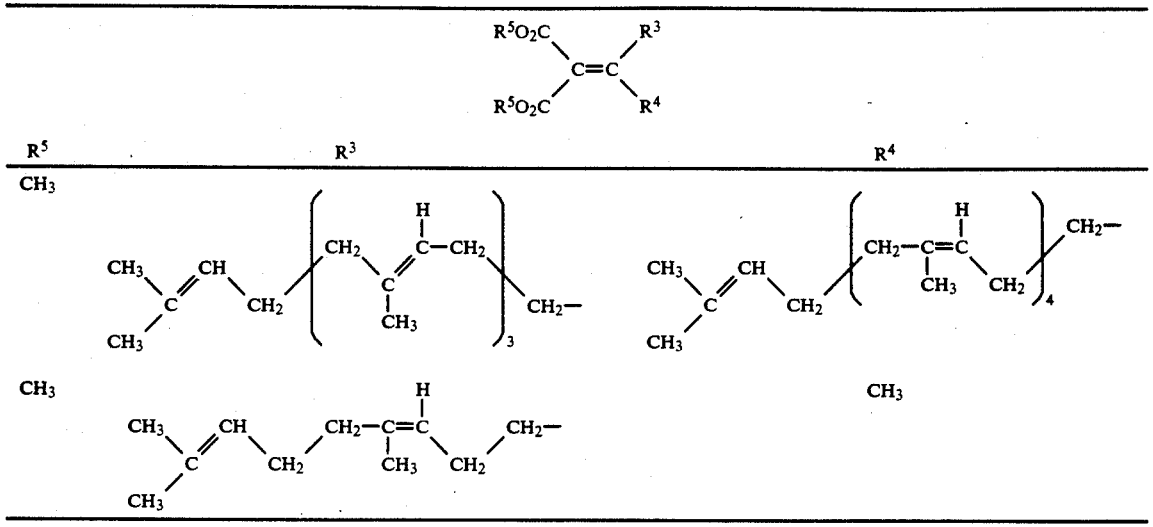

The above decarboxylates may be prepared employing procedures known in the art, for example as described in W. Lehnert Tetrahedron 1973, 29, 635-638.

The following working examples represent preferred embodiments of the present invention. Unless otherwise indicated, all temperatures are expressed in degrees centigrade.

EXAMPLE 1

(E,E,E)-2-(4,8-Dimethyl-3,7-nonadienyl)-2-methyl-3-(2,6,10-trimethyl-1,5,9-undecatrienyl)-1,1-cyclopropanedicarboxylic acid, dimethyl ester

A.

(E)-(1,5,9-Trimethyl-4,8-decadienylidene)-propanedioic acid, dimethyl ester

To 200 mL of tetrahydrofuran at 0° C. under argon was added over 45 minutes a solution of 102 mL (102 mmol, 2 equiv) of 1 M titanium (IV) chloride in $CH_2Cl_2$, resulting in the formation of a granular, yellow precipitate. The reaction mixture was treated with 11.5 mL (51 mmol) of geranyl acetone and 5.8 mL (51 mmol) of dimethyl malonate, followed by the addition over one hour of a solution of 16.5 mL (204 mmol, 4 equiv) of pyridine in 35 mL of tetrahydrofuran. The resulting brown, sludgy mixture was stirred 16 hours at room temperature, then quenched with 25 mL of water and diluted with 600 mL of diethyl ether. The organic phase was washed with 100 mL of saturated $NaHCO_3$, 100 mL of $H_2O$ and 100 mL of brine, dried over $MgSO_4$ and evaporated to give 15.6 g of crude material as an orange oil. Purification by flash chromatography on 1.5 kg of silica gel, eluted with 2:98 ethyl acetate: hexane provided 9.34 g (60%) of title diester as a yellow oil.

TLC Silica gel (5:95 ethyl acetate: hexane) $R_f$=0.24.
IR ($CCl_4$) 2968, 2951, 2926, 2919, 2857, 1723, 1635, 1434, 1376, 1284, 1244, 1221, 1151, 1063 cm$^{-1}$.
$^1$H-NMR ($CDCl_3$, 270 MHz): δ 5.13 (t, 1H, J=7.0 Hz), 5.09 (t, 1H, J=7.0 Hz), 3.76 (s, 6H), 2.38 (t, 2H, J=7.0 Hz), 2.20 (q, 2H, J=7.0 Hz), 2.08 (s, 3H), 1.9–2.1 (m, 4H), 1.68 (s, 3H), 1.61 (s, 3H), 1.60 (s, 3H), ppm.
Mass Spec (Cl—$CH_4$/$N_2O$,=ions) m/e 337 ($M+C_2H_5$), 309 ($M+H$), 307 ($M+H-H_2$).
Anal. Calc'd for $C_{18}H_{28}O_4$: C, 70.10; H, 9.15.
Found: C, 70.16; H, 9.43.

B. (E,E)-3,7,11-Trimethyl-2,6,10-dodecatrienyl bromide (Farnesyl bromide)

A solution of 1.00 g (4.5 mmol) of E,E-farnesol (Aldrich, further purified by flash chromatography) in 10 mL of distilled ether at 0° C. under argon in the dark was treated dropwise with a solution of 195 μL (2.05 mmol, 0.45 eq.) of $PBr_3$ in 2 mL of ether. The resultant mixture was stirred at 0° C. for one hour, then quenched with water and separated. The organic phase was washed with 5 mL of $H_2O$, 5 mL of saturated $NaHCO_3$, and 5 mL of brine, dried over $Na_2SO_4$ and evaporated to give 1.26 g (98%) of crude bromide as a clear oil. TLC Silica (2:8 ethyl acetate:Hexane) $R_f$=0.69 (decomposes).

$^1$H NMR ($CDCl_3$): δ 5.52 (t, 1H, J=8.5 Hz), 5.08 (m, 2H), 4.01 (d, 2H), 1.9–2.2 (m, 8H), 1.73 (s, 3H), 1.68 (s, 3H), 1.60 (s, 6H) ppm.

C. (E,E)-(3,7,11-Trimethyl-2,6,10-dodecatrienyl) (trifluoromethyl)sulfone

A mixture of 12.20 g (42.8 mmol) of Part B farnesyl bromide, 8.0 g (52 mmol, 1.2 equiv) of potassium trifluoromethylsulfinate (Parrish Chemical) and 1.00 g (4.3 mmol, 0.1 equiv) of 18-crown-6 in 200 mL of dry dimethylformamide was stirred for 66 hours. The dimethylformamide was evaporated at reduced pressure with minimal warming. The residue was dissolved in 600 mL of diethyl ether and washed with three 70 mL portions of $H_2O$ and 70 mL of brine, dried over $MgSO_4$ and evaporated. Purification by flash chromatography on 200 g of Merck 9385 silica eluted with 15:85 $CH_2Cl_2$: hexane provided 1.35 g of mixed fractions and 9.02 g (63%) of pure product. The mixed fractions were rechromatographed on 60 g of silica gel, eluting with 15:85 $CH_2Cl_2$: hexane to provide 0.95 g (7%) of pure title product. The two portions of pure title triflone product were combined: 9.97 g (70%) of a pale yellow oil.

TLC Silica gel (15:85 $CH_2Cl_2$: hexane) $Rf_2$=0.10.
IR ($CCl_4$) 2968, 2924, 2917, 2855, 1660, 1447, 1372, 1223, 1211, 1197, 1123, 623 cm$^{-1}$.
$^1$H-NMR ($CDCl_3$, 270 MHz): δ 5.25 (t, 1H, J=7.62 Hz), 5.08 (m, 2H), 3.93 (d, 2H, J=7.62 Hz), 1.9–2.2 (m, 8H), 1.78 (s, 3H), 1.68 (s, 3H), 1.60 (s, 6H) ppm.

Mass Spec (CI—NH$_3$,+ions) m/e 356 (M+NH$_4$), 338 (M), 69.

Anal. Calc'd for C$_{16}$H$_{25}$F$_3$O$_2$S: C, 56.78; H, 7.45; F, 16.84.

Found: C, 56.86; H, 7.54; F, 16.41.

D.
(E,E,E)-2-(4,8-Dimethyl-3,7-nonadienyl)-2-methyl-3-(2,6,10-trimethyl-1,5,9-undecatrienyl)-1,1-cyclopropanedicarboxylic acid, dimethyl ester A solution of 9.930 g (29.3 mmol) of Part C triflone and 10.2 mL (59.6 mmol, 2 equiv) of hexamethylphosphoramide (distilled) in 150 mL of tetrahydrofuran at −78° C. under argon was treated over 0.5 hours with a solution of 20.5 mL (32.5 mmol, 1.1 equiv) of 1.6 M n-butyllithium in hexanes. After 0.5 hours at −78° C., a solution of 9.96 g (32.5 mmol, 1.1 equiv) of Part A diester in 5 mL of tetrahydrofuran was added over 0.5 hours. The reaction mixture was stirred for one hour at −78° C. and five hours at 0° C., then quenched with NH$_4$Cl and diluted with 700 mL of diethyl ether. The organic phase was washed with five 50 mL portions of H$_2$O, and 50 mL of brine, dried over MgSO$_4$ and evaporated to yield 18.36 g of crude product. Purification by flash chromatography on 1 kg of silica gel, eluted with 3:97 diethyl ether:hexane provided 12.67 g (84%) of pure title diester as a clear, colorless oil. The title diester was isolated as an inseparable mixture of isomers of approximately 1.6:1 (1):(2). These assignments were made on the basis of NOE studies on the mixture.

TLC Silica gel (1:1 toluene:hexane) R$_f$ 0.17.

IR (CCl$_4$) 2966, 2949, 2925, 2916, 2855, 1731, 1448, 1434, 1382, 1377, 1296, 1239, 1196, 1164, 1103, 1069 cm$^{-1}$.

$^1$H-NMR C$_6$D$_6$, 400 MHz): δ 5.40 (dd, J=8, 1.1 Hz), 5.35 (d, J=8 Hz), 5.21 (m, 4H), 3.41 (s), 3.40 (s), 3.38 (s), 3.37 (s), 2.81 (d, J=8 Hz), 2.75 (d, J=8 Hz), 2.0–2.2 (m, 14H), 1.72 (s), 1.71 (s), 1.67 (s, 6H), 1.58, 1.56, 1.55 (three s, 12H), 1.44 (s), 1.26 (s) ppm.

Anal. Calc'd for C$_{33}$H$_{52}$O$_4$: C, 77.30; H, 10.22,

Found: C, 77.08; H, 10.43.

EXAMPLE 2
(E,E)-2,2-Dimethyl-3-(2,6,10-trimethyl-1,5,9-undecatrienyl)-1,1-cyclopropanedicarboxylic acid, dimethyl ester A solution of 600 mg (1.77 mmol) of Example 1, Part C farnesyl triflone and 615 μL (3.54 mmol, 2 equiv.) of hexamethylphosphoramide (distilled) in 8 mL of tetrahydrofuran was treated over four minutes with a solution of 1.25 mL (1.95 mmol, 1.1 equiv.) of 1.6 M n-butyllithium in hexanes, to provide a pale yellow solution. After 0.5 hours, a solution of 337 mg (1.95 mmol, 1.1 equiv.) of (1-methylethylidene)propanedioic acid, dimethyl ester in 2 mL of tetrahydrofuran was added dropwise. The reaction mixture was stirred for one hour at −78° C. and three hours at 0° C., then quenched with saturated NH$_4$Cl and diluted with 80 mL of diethyl ether. The organic phase was washed with five 20 mL portions of H$_2$O and 20 mL of brine, dried over MgSO$_4$, and evaporated to yield 727 mg of crude title product. Purification by flash chromatography on 70 g of silica gel, eluted with 2:98 ethyl acetate/hexanes provided 522 mg (81%) of the title cyclopropane as a clear, colorless oil.

TLC Silica gel (5:95 ethyl acetate/hexanes) R$_f$=0.37.

IR (CCl$_4$) 2950, 2926, 2855, 1731, 1459, 1445, 1434, 1379, 1306, 1289, 1242, 1196, 1117, 1101, 1073 cm$^{-1}$.

$^1$H-NMR (CDCl$_3$, 270 MHz) δ 5.10 (m, 2H), 5.01 (d, 1H, J=8.20 Hz), 3.73 (s, 3H), 3.69 (s, 3H), 2.45 (d, 1H, J=8.20 Hz), 1.9–1.2 (m, 8H), 1.73 (s, 3H), 1.68 (s, 3H), 1.60, (s, 6H), 1.27 (s, 3H), 1.24 (s, 3H) ppm.

Mass spec. (CI—CH$_4$/N$_2$O,+ions) m/e 417 (M+C$_3$H$_5$), 405 (M+C$_2$H$_5$), 377 (M+H), 345, 313.

Anal. Calc'd for C$_{23}$H$_{36}$O$_4$: C, 73.37; H, 9.64.

Found: C, 73.47; H, 9.63.

The compounds prepared in accordance with the method of the invention may be used to prepare monocarboxylates as described in parent application Ser. No. 573,507, now U.S. Pat. No. 5,095,136, which may be employed to prepare squalene synthetase inhibitors, using techniques as disclosed in Capson et al, supra, which are useful in inhibiting cholesterol biosynthesis, and may be used to prepare insecticides in accordance with Arlt et al, supra.

What is claimed is:

1. A method for preparing an isoprenoid cyclopropane 1,1-dicarboxylate of the structure where R$^1$, R$^2$, R$^3$ and R$^4$ are the same or different and are independently selected from CH$_3$ or where n is 0 to 3 and R$^5$ is lower alkyl, which comprises treating an allylic fluorinated sulfone of the structure where R$_f$ is CF$_3$(CF$_2$)$_m$, where m is 0 to 5, and R$^1$ and R$^2$ are as defined above, with a strong base at a temperature within the range of from about −80° to about −40°

C. to form the carbonion of the sulfone having the structure

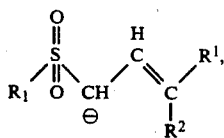

after all strong base is reacted, reacting the carbanion of the sulfone with an alkene 1,1-dicarboxylate of the structure

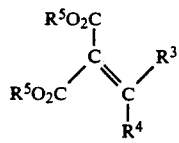

wherein $R^3$, $R^4$ and $R^5$ are as defined above, at a reduced temperature of within the range of from about $-80°$ to about $-40°$ C., to form the intermediate

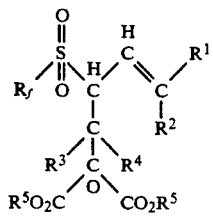

and subjecting the intermediate to a temperature of within the range of from about 25° C. to about 0° C. to form the isoprenoid cyclopropane 1,1-carboxylate.

2. The method as defined in claim 1 wherein the strong base is n-butyllithium or lithium diisopropylamide.

3. The method as defined in claim 1 wherein the treatment of the allylic fluorinated sulfone with the strong base is carried out in the presence of an anion activator.

4. The method as defined in claim 3 wherein the anion activator is hexamethylphosphoramide or N,N-dimethylpropyleneurea.

5. The method as defined in claim 1 wherein the reaction is carried out in the presence of a solvent which is tetrahydrofuran (THF), or diethyl ether.

6. The method as defined in claim 4 wherein the reaction is carried out in the presence of n-butyllithium, hexamethylphosphoramide, and tetrahydrofuran.

7. The method as defined in claim 1 wherein the allylic fluorinated sulfone is employed in a molar ratio to the alkene 1,1-dicarboxylate of within the range of from about 0.7:1 to about 1.3:1.

8. The method as defined in claim 1 wherein one of $R^3$ and $R^4$ is methyl.

9. The method as defined in claim 1 wherein at least one of $R^3$ and $R^4$ is

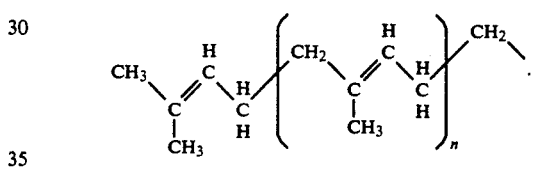

10. The method as defined in claim 9 wherein n is 2.

* * * * *